United States Patent [19]

Regalbuto

[11] Patent Number: 4,932,239
[45] Date of Patent: Jun. 12, 1990

[54] STANDARD TARGET FOR EXPLOSIVE CHARGE TESTING

[75] Inventor: John A. Regalbuto, Fort Worth, Tex.

[73] Assignee: Jet Research Center, Inc., Alvarado, Tex.

[21] Appl. No.: 241,813

[22] Filed: Sep. 1, 1988

Related U.S. Application Data

[62] Division of Ser. No. 99,863, Sep. 22, 1987, abandoned.

[51] Int. Cl.⁵ .............................................. G01N 33/22
[52] U.S. Cl. ............................................ 73/35; 73/12
[58] Field of Search .................. 73/35, 12, 167, 84, 73/866.4

[56] References Cited

U.S. PATENT DOCUMENTS

| | | | |
|---|---|---|---|
| 1,375,077 | 4/1921 | Buckman et al. | |
| 1,684,739 | 9/1928 | Minton. | |
| 1,886,249 | 11/1932 | Bensing. | |
| 2,471,227 | 5/1949 | Marshall | 73/15.6 |
| 2,647,397 | 8/1953 | Dietert | 73/38 |
| 2,791,120 | 7/1952 | Dietert et al. | 73/432 |
| 2,916,913 | 12/1959 | Stevenson | 73/94 |
| 2,988,994 | 6/1961 | Fleischer et al. | 73/12 |
| 3,130,575 | 4/1964 | Rogers | 73/12 |
| 4,047,425 | 9/1977 | Handy et al. | 73/94 |
| 4,115,345 | 9/1978 | Bushey | 524/443 |
| 4,152,941 | 5/1979 | Abou-Sayed et al. | 73/799 |
| 4,283,319 | 8/1981 | Konii et al. | 523/145 |
| 4,379,401 | 4/1983 | San Miguel | 73/35 |

FOREIGN PATENT DOCUMENTS 96782  8/1981  Japan ................. 524/443

*Primary Examiner*—John Chapman
*Attorney, Agent, or Firm*—Robert A. Kent; David J. Alexander

[57] ABSTRACT

A method of testing an explosive charge using a uniform shaped charge testing standard that is simulative of naturally occuring Berea sandstone test specimens. A quantity of zircon sand is mixed with from 3% to 8% by weight of the total mixture of a phenolic resin and then agitated to achieve desired density of the mixture for subsequent controlled heating to cure the mass into a molded shape suitable for explosives testing. An explosive shaped charge is detonated in the proximity of the standard, and the penetration of the shaped charge on the standard is measured.

11 Claims, 1 Drawing Sheet

STANDARD TARGET FOR EXPLOSIVE CHARGE TESTING

This is a division of application Ser. No. 099,863, filed Sept. 22, 1987, now abandoned.

BACKGROUND OF THE INVENTION

1. Field of the Invention

The present invention relates to a method for forming an article of manufacture that is an explosives testing standard that may be molded variously to achieve different sizes and configurations while having uniform texture and predetermined density.

2. Description of the Prior Art

The prior art reveals relatively little attention toward construction of testing standards to evaluate the penetration of shaped charge jets into porous rock as would be characteristic of oil well perforators. U.S. Pat. No. 4,152,941 relates to measuring of the fracture toughness of rock in a simulated environment wherein a rock specimen is pressurized internally while simultaneously exerting increasing external horizontal stress. This is a destructive testing procedure which is effected to derive data relative to the actual rock while the environment is that which is simulated. The U.S. Pat. No. 1,684,739 relates to a zircon refractory including granular zircon and an organic binder that has been shaped and fired as desired. The zircon is shaped under considerable pressure and then fired at very high temperatures in order to form a stable refractory material.

U.S. Pat. No. 1,886,249 relates to the use of zircon sand and a suitable binder to form cores for molds. The binder material may be an organic material such as flour and dextrine mixed with water to provide sufficient plasticity and binding strength for the zircon sand to hold its shape. U.S. Pat. No. 2,647,397 relates to a method for forming a test specimen of standardized type as compacted in a cylindrical mold to form a solid of particular hardness characteristics. In this case, the compacted material undergoing compression is also the material that is being tested for certain green characteristics such as strength, deformation and permeability.

SUMMARY OF THE INVENTION

The present invention relates to an improved standard specimen for testing of explosive shaped charges or the like. The invention consists of mixing predetermined amounts of zircon sand and a suitable phenolic resin binder for subsequent firing at a known elevated temperature for a selected duration thereby to impart known characteristics of density, compressive strength and compressibility to the specimen in uniform manner. The invention enables a more uniform explosive perforator test specimen having the basic characteristics of the present industry standard, Berea sandstone, naturally existent in certain parts of the United States.

Therefore, it is a object of the present invention to provide an explosive perforator test specimen having known characteristics and uniform density throughout.

It is another object of the invention to provide a more uniform explosive perforator test specimen at a reduced cost per specimen.

It is also an object of the invention to provide a method for forming a test specimen wherein the density characteristics are accurately adjusted and maintained to a desired value.

It is yet further an object of the present invention to provide an explosive perforator test specimen that provides more accurate target penetration data.

Finally, it is an object of the invention to provide a perforator test target that accurately simulates a Berea sandstone standard of selected density.

Other objects and advantages of the invention will be evident from the following detailed description when read in conjunction with the accompanying drawings which illustrate the invention.

DETAILED DESCRIPTION OF THE INVENTION

Figure 1:
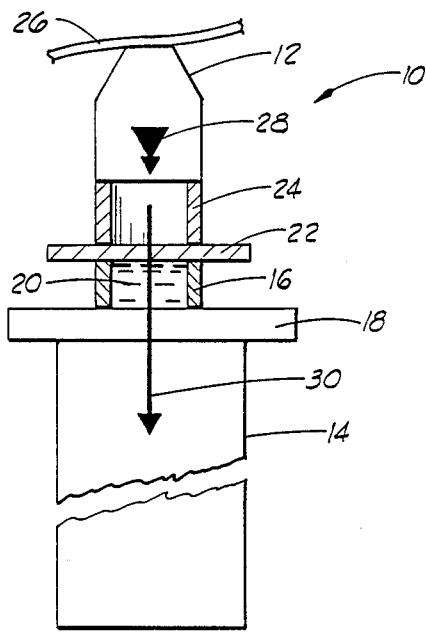
FIG. 1 is a side view with parts shown in vertical section of a shaped charge testing set-up as currently known and used.

FIG. 1 illustrates a testing procedure for shaped charges that may be considered to be in the prior art. A test set up 10 is configured to employ a particular explosive charge, in this case a shaped charge 12, adapted for penetration as directed into a standard type of test specimen 14. The test specimen 14 as currently used for evaluation of oilwell perforator charges is Berea sandstone, a naturally occuring rock that is quarried from a single location in the United States. The compressive strength of the Berea sandstone can vary from 4,000 to 11,000 PSI compressibility, and quite often the rock may contain bedding planes which make its properties vary with orientation.

The testing apparatus 10 includes certain other intermediary structures that are utilized for simulating tubing and/or casing structures and well fluids that may be present at a point of perforation. Thus, a steel ring 16 is glued on top of a rupture plate 18 by means of a suitable water proof glue and this assembly is centered over the end of test specimen 14. Water 20 is then filled within ring 16 and retained therein by a steel plate 22. A second spacer ring 24 of slightly greater length is then placed on plate 22 in coaxial alignment with ring 16 and the charge 12 undergoing test is placed thereon. The charge 12 consists of selected case and cone portions characteristic of shaped charges, and a suitable detonating cord 26 is affixed as by taping to the top of shaped charge 12 to enable detonation.

A shaped charge 12, a perforator type, is ignited by detonating cord 26 and the explosive force tends to concentrate the shaped charge liner along the central axis as shown by arrow 28 to direct a penetrator or jet along the direction of arrow 30. The depth of penetration of the shaped charge jet into the test specimen 14 will depend upon the size and type of shaped charge 12 as well as the support array and thicknesses of plates 18 and 22. Accurate data are continually maintained for each type of shaped charge to define the explosive capabilities in terms of inches penetration, entry hole diameter in inches, metal burr height, etc.

Figure 2:
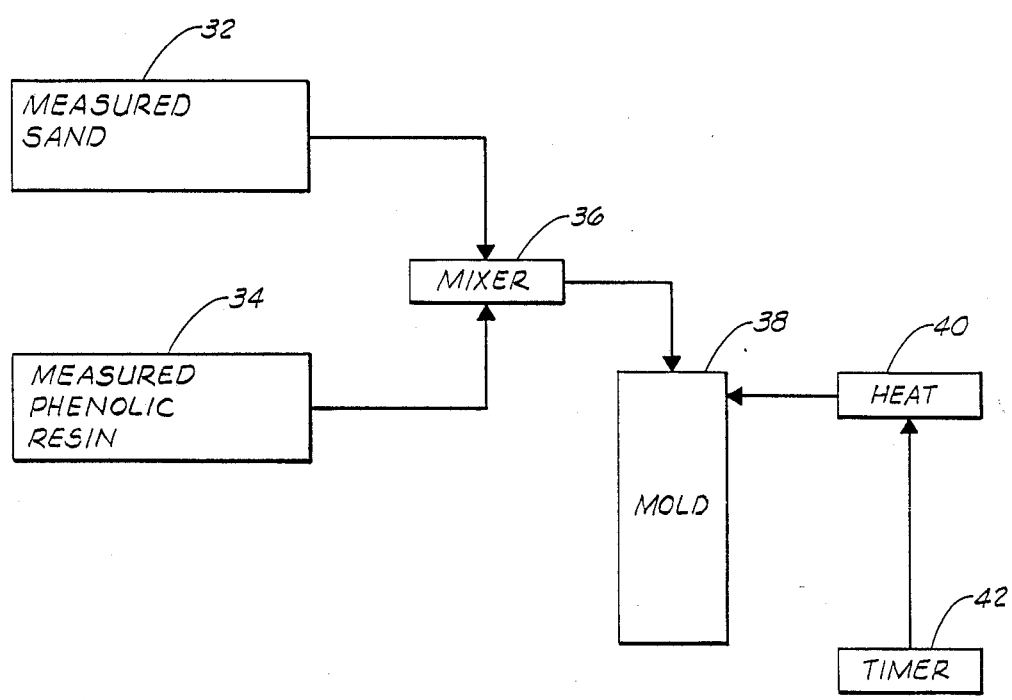
FIG. 2 is a procedural block diagram showing the manner in which the invention is formed and finished.

As shown in FIG. 2, a standard target constructed in accordance with the invention, having reliably uniform properties and characteristics, is made by certain combining of sand and phenolic resin components. A measured amount of sand and a measured amount of phenolic resin are placed in a suitable mixer stage 36. At stage 32, it is preferable to use zircon sand, a naturally occuring zirconium silicate having a relatively high specific gravity. In stage 34 a measured amount of phenolic resin is added and stage 36 effects mixing of the constituents. The zircon sand may be mixed with the phenolic resin in proportions of 3% to 8% resin with 97% to 92% sand, respectively. The phenolic resin is preferably a novalac, a thermoplastic phenolformaldehyde type of resin. The novalac type resins have the property that they convert to cured, cross-linked structures by heating in the 200° to 400° F. range. A suitable type of resin is that known as MD-34, available from Borden Chemical, Division of Borden, Inc., Columbus, Ohio.

Mixing at stage 36 may be carried out using any standard dry mixing procedure such as mullers, spiral type mixers, tumblers or equivalents. Mixing time will vary with the type of mixer used and it may be advisable to add a small amount of fuel oil or kerosene to reduce dust while mixing. The mixture at stage 36 is then finally compacted as by agitation or vibration until it exhibits a density in the range of 2.7 to 2.8 grams per cubic centimeter.

As presently processed, the mold stage 38 functions to compact the mixture prior to heat subjection. Thus, a standard target is formed using a four inch outside diameter metal tube with a bottom end closed off by foil material such as aluminum foil. The empty tube is then placed foil bottom down on a tray or support and the tube is filled with a quantity of the zirconia-phenolic resin mixture to a desired depth. Thereafter, the mold form and sand are agitated to effect compaction to the desired density range and the mixture is ready for application of heat.

Heat is then applied as at stage 40 using a suitable oven equipment to bring the temperature into the range of 300° to 500° F., the exact temperature depending upon the time of heating. A timer 42 controls time of molding. The time and temperature of the heating process will be a function of the thickness of the specimen desired. Final molding of a standard target results in a uniform solid with uniform porosity in the form of a cylinder having four inches diameter and length of twelve to twenty-three inches. This, of course, may be varied for specific testing purposes but for shaped charged perforator elements it has become a standard. The standard target approximates naturally occurring sandstone and has a density of 2.7–2.8 grams per cubic centimeter and a compressive strength greater than 5,000 PSI but this can be varied from about 4,000 up to 11,000 PSI.

When the standard target is subjected to perforation by an oil-well type shaped charge jet, the material exhibits a "crushed zone" along the axis. This type of break down is also characteristic of the similar Berea sandstone standards used heretofore. Thus, some comparison data illustrates some relative differences in explosive jet penetration in inches between the zircon standards and the dry Berea specimens.

| TYPE | EXPLOSIVE | Zirconia + % Phenolic Resin | | | DRY BEREA |
| --- | --- | --- | --- | --- | --- |
| | | 3% | 5% | 8% | |
| 3⅜" 22.7 gms. | PYX | 15.03" | 13.65" | 11.59" | 12.50" |
| 4" 32 gms. | RDX | — | 15.85" | 14.95" | 15.76" |

Each of the materials was tested in a set-up such as shown in FIG. 1 wherein the charges of selected weight and length and compressed bulk were detonated to direct the discharged jet into a target 14, either the zircon plus phenolic resin cured mixture or a dry Berea target. Noting the data, the depth of penetration of the discharge jet became progressively less through the zircon plus eight percent phenolic mixture, and the discharge jet through dry Berea at 12.50 lies within the same range. It should be kept in mind, however, that two different targets of natural Berea sandstone having seemingly similar properties can vary considerably as to the penetration allowed the discharge jet. Similarly, the heavier charge of RDX explosive shows favorable comparison between the discharged jet penetration of the zircon plus phenolic resin mixtures and the dry Berea sandstone. The major difference is that the zircon standards from controlled batch mixtures will exhibit much more uniformity in response. A large plurality of targets can be molded from a single batch mix and all will have the same uniform properties of physical structure.

The foregoing discloses a novel form of uniform standard that may be utilized industry wide for evaluation of such as oil well shaped charge perforators. Control of the sand type, the percentage of resin, curing time and curing temperature, results in a material that has uniform physical properties and can maintain such over the production span of many units of specimens formed from the material. It is also contemplated that the zircon compounds may be replaced by any of a number of other heavy minerals that have high crystal densities, e.g., ZIRCORE®, hematites, itabarite and others. In particular, ZIRCORE®, available from DuPont Co., is a foundry sand that is well suited for molding of uniform property specimens.

Changes may be made in combination and arrangement of elements as heretofore set forth in the specification and shown in the drawings; it being understood that changes may be made in the embodiments disclosed without departing from the spirit and scope of the invention as defined in the following claims.

What is claimed is:

1. A method of testing an explosive charge comprising:
    detonating an explosive shaped charge in the proximity of a target comprising a molded article produced by admixed a quantity of phenolic resin with a particulate, the admixture being compacted in a mold to yield a product having a specific gravity in the range of from about 2.7 to about 2.8, the molded compacted mixture then being heated to an elevated temperature for a sufficient duration to form a target having uniform density and compression properties;
    measuring at least one feature of the penetration of the shaped charge on the target;
    determining the explosive capability of the shaped charge from the measured feature of the penetration.

2. The method of claim 1 wherein the phenolic resin is a novalac resin which is present in an amount of from about 3 to about 8% by weight of the target.

3. The method of claim 1 wherein the phenolic resin is a novalac resin which is present in an amount of from about 5 to about 8% by weight of the target.

4. The method of claim 1 wherein said particulate is a zircon-containing sand.

5. The method of claim 1 wherein said particulate includes at least one member selected from the group consisting of a zircon-containing sand, hematite and itabarite.

6. The method of claim 1 wherein said elevated temperature is in the range of from about 300° F. to about 500° F.

7. The method of claim 1 wherein the duration of said heating is from about ten seconds to about 4 hours.

8. A method of testing an explosive shaped charge comprising:
    positioning a first steel plate upon a target comprising a molded article produced by admixing a quantity of a phenolic resin with a particulate, the admixture being compacted in a mold to yield a product having a specific gravity in the range of from about 2.7 to about 2.8, the molded compacted admixture then being heated to an elevated temperature for a sufficient duration to form a target having uniform density and compression properties;
    positioning a quantity of aqueous fluid adjacent said first steel plate which is confined within a retainer means:
    positioning a second steel plate adjacent said retainer means whereby it is aligned with said target, first steel plate and retainer means;
    positioning shaped charge means adjacent said second steel plate, said shaped charge being spaced a predetermined distance from said second steel plate by a spacing means;
    detonating said shaped charge means whereby the explosive force is directed against said second steel plate such that the explosive force penetrates the second steel plate, the aqueous fluid retainer means and first steel plate to enter said target;
    measuring at least one feature of the penetration of the charge on the target; and
    determining the explosive capability of said shaped charge from the measured feature of the penetration.

9. The method of claim 8 wherein the measured feature of the target comprises at least one member selected from the group consisting of depth of penetration, entry hole diameter and metal burr height.

10. The method of claim 8 wherein the phenolic resin is a novalac resin which is present in an amount of from about 3 to about 8% by weight of the target.

11. The method of claim 8 wherein said particulate includes at least one member selected from the group consisting of a zircon-containing sand, hematite and itabarite.

* * * * *